United States Patent
Finlay

(10) Patent No.: US 9,649,020 B2
(45) Date of Patent: May 16, 2017

(54) CONTROL ASSEMBLY

(75) Inventor: Patrick Armstrong Finlay, Beaconsfield (GB)

(73) Assignee: Freehand 2010 Limited, Guildford (GB)

( * ) Notice: Subject to any disclaimer, the term of this patent is extended or adjusted under 35 U.S.C. 154(b) by 1498 days.

(21) Appl. No.: 12/186,450

(22) Filed: Aug. 5, 2008

(65) Prior Publication Data
US 2009/0112056 A1   Apr. 30, 2009

(30) Foreign Application Priority Data

Oct. 26, 2007 (GB) .................................. 0721121.2

(51) Int. Cl.
A61B 1/00 (2006.01)
A61B 1/04 (2006.01)
(Continued)

(52) U.S. Cl.
CPC ........ *A61B 1/3132* (2013.01); *A61B 1/00147* (2013.01); *A61B 34/70* (2016.02); *A61B 2017/3409* (2013.01)

(58) Field of Classification Search
USPC ....... 600/102, 227–229, 231, 417, 429, 114; 606/1, 53–56, 108, 130
See application file for complete search history.

(56) References Cited

U.S. PATENT DOCUMENTS 5,417,210 A * 5/1995 Funda et al. .................. 600/425
6,024,695 A 2/2000 Taylor et al.
(Continued)

FOREIGN PATENT DOCUMENTS

EP 0571827 5/1993
EP 1815950 A1 8/2007
(Continued)

OTHER PUBLICATIONS

Summons to Attend Oral Proceedings Pursuant to Rule 115(1) EPC regarding corresponding European Patent Application No. 081043044, dated May 4, 2015.
(Continued)

*Primary Examiner* — Ryan Henderson
(74) *Attorney, Agent, or Firm* — Lewis, Reese & Nesmith, PLLC

(57) ABSTRACT

A control assembly for manipulating the movement of an endoscopic instrument includes an endoscopic instrument mounting arrangement adapted to receive an endoscopic instrument, three driving arrangements, and three independent control elements. The mounting arrangement offers only three independent degrees of freedom of movement of an endoscopic instrument received by the arrangement, each degree of freedom of movement being about or along a respective axis. Each of the three driving arrangements are configured to drive the endoscopic instrument in only one of the degrees of freedom of movement. The three independent control elements are configured to receive user input, such that the actuation of each of the three independent control elements regulates one of three corresponding control signals, each control being a respective one of the driving arrangements independent of the other two driving arrangements in accordance with the user input.

10 Claims, 3 Drawing Sheets

(51) Int. Cl.
*A61B 5/05* (2006.01)
*A61B 17/00* (2006.01)
*A61F 11/00* (2006.01)
*A61B 19/00* (2006.01)
*A61B 1/313* (2006.01)
*A61B 17/34* (2006.01)
*A61B 34/00* (2016.01)

(56) References Cited

U.S. PATENT DOCUMENTS

| | | | |
|---|---|---|---|
| 6,406,472 B1 * | 6/2002 | Jensen | 606/1 |
| 6,497,651 B1 * | 12/2002 | Kan et al. | 600/114 |
| 8,231,610 B2 * | 7/2012 | Jo et al. | 606/1 |
| 2002/0040217 A1 | 4/2002 | Jinno | |
| 2002/0156345 A1 * | 10/2002 | Eppler | A61B 1/00147 600/114 |
| 2003/0229338 A1 * | 12/2003 | Irion et al. | 606/1 |
| 2005/0234435 A1 * | 10/2005 | Layer | 606/1 |
| 2006/0100501 A1 * | 5/2006 | Berkelman et al. | 600/415 |
| 2008/0058776 A1 * | 3/2008 | Jo | A61B 19/22 606/1 |
| 2010/0185212 A1 * | 7/2010 | Sholev | 606/130 |
| 2012/0029277 A1 * | 2/2012 | Sholev | 600/102 |

FOREIGN PATENT DOCUMENTS

| | | |
|---|---|---|
| JP | 2000350735 A | 12/2000 |
| JP | 2007260431 A | 10/2007 |
| WO | WO 97/00649 | 1/1997 |
| WO | WO 2006/111966 | 10/2006 |
| WO | WO 2007/045810 | 4/2007 |
| WO | WO 2008/001003 A2 | 1/2008 |
| WO | WO 2008/001003 A3 | 6/2008 |

OTHER PUBLICATIONS

Provision of the Minutes in Accordance with Rule 124(4) EPC regarding corresponding European Patent Application No. 08104304.4, dated Nov. 3, 2015.

* cited by examiner

CONTROL ASSEMBLY

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The present invention relates to a control assembly for manipulating the movement of an endoscopic instrument. Embodiments of the present invention relate to the control assembly and a method of manufacturing the control assembly.

2. Description of Related Art Including Information Disclosed Under 37 CFR 1.97 and 37 CFR 1.98

There are a number of occasions during which it is necessary to view and work on remote or inaccessible sites. For example, during a surgical operation, it is sometimes necessary to operate on organs which are within the human body. In an industrial context, certain parts of a machine can be practically inaccessible to a maintenance engineer without dismantling the machine to gain access to the parts of interest.

In the example of a surgical operation, a surgeon may wish to carry out surgery through as small an incision as possible to reduce scarring and trauma to the patient. In addition, small incisions will reduce the risk of infection and can lead to reductions in post-operative recovery times for the patient.

Thus, there is a requirement for instruments and imaging devices, with relatively small external dimensions, which can be maneuvered through small orifices to allow access to remote or inaccessible sites.

To this end, endoscopic instruments have been developed for use in surgical operations. These instruments may include, among others, endoscopes, laparoscopes, endoscopic clamps and the like.

Endoscopes comprise a rigid tubular body. The proximal end of the endoscope is attached to a camera, and the distal end is inserted into a patient. One or more optical fibers, which run through the tubular body, provide an optical link between the distal end and the proximal end of the endoscope or laparoscope. Thus, an endoscope can be used in combination with a camera to view the internal organs of a patient during surgery through a small incision. Other endoscopic instruments have a similar construction, with a tool at the distal end and an actuator at the proximal end.

Traditionally, these instruments have been held in place by an assistant who moves the instrument in response to instructions from the surgeon (who may also be manipulating a similar instrument). Recently, a number of mechanized and robotic devices have been developed to hold and maneuver endoscopes to allow the surgeon to control the camera directly, using, for example, voice commands or head movements. Similar mechanized and robotic devices have been developed for other endoscopic instruments.

One such device is described in U.S. Pat. No. 6,024,695. This document describes a device, which includes a manipulator for manipulating a surgical instrument relative to a patient's body. The manipulator can be manually or may be computer actuated. The robot is complex and is able to move in a large number of different axes, although some of these axes may be "locked" to limit the movement. In order to allow for computer actuated control of the robot a number of motors are provided.

The large number of possible axes of movement is a hindrance to the ease of operation of the robot during surgery. For example, in order to move a surgical instrument from one position to another within the patient, there are several possible movements which could achieve the same general result but which have an effect upon how future movements might be achieved.

Moreover, the positioning of the robot in one of the possible axes may have an effect upon how the robot is able to move in the other axes. For example, the document discloses a "ball and socket" joint between two parts of the robot and a sliding joint beneath the ball and socket joint. If the ball and socket joint is in a first position then movement of the sliding joint may be operative in a different direction with respect to a patient when compared with the same sliding joint when the ball and socket joint is in a second position.

In a surgical operation, if movements of an endoscopic instrument are not confocal at the incision then the patient's skin may become stretched, distorted, or torn by the laparoscope at the incision.

Thus, when controlling robots of this type, it is necessary to provide an arrangement which is capable of translating the movement of the endoscopic instrument which is desired by the operator into a complex series of movements in the various axes of movement of the robot to ensure that the desired movement is achieved in a substantially confocal manner with respect to the incision. These complex series of movements are known as compound movements and require computationally expensive kinematic calculations based upon a number of factors to determine the relative motion of each robotic joint. Factors which must be taken into consideration include the geometry of the robot, its joints and limbs, the axes in which movement is possible, and the speed at which any movement can be carried out.

Accordingly, robots for use in surgical operations are large complex devices which require significant processing power in order to operate successfully.

Similar problems exist in other fields, such as industrial applications.

BRIEF SUMMARY OF THE INVENTION

The present invention seeks to ameliorate at least some of the problems associated with the prior art.

Accordingly, an aspect of the present invention provides a control assembly for manipulating the movement of an endoscopic instrument. The control assembly comprises: an endoscopic instrument mounting arrangement adapted to receive an endoscopic instrument and offer only three independent degrees of freedom of movement of an endoscopic instrument received by the arrangement, each degree of freedom of movement being about or along a respective axis; three driving arrangements each being configured to drive the endoscopic instrument in only one of the degrees of freedom of movement; and three independent control elements configured to receive user input, such that the actuation of each of the three independent control elements regulates one of three corresponding control signals which each control a respective one of the driving arrangements independently of the other two driving arrangements in accordance with the user input.

Advantageously, endoscopic instrument is an endoscope.

Preferably, the endoscopic instrument mounting arrangement comprises: a curved track which is configured so as to be rotatable about a rotation axis with respect to a support structure of the control assembly, the curved track having a center of curvature along the rotation axis; and an endoscopic instrument mount configured to receive an endoscopic instrument, move along the curved track, and move the instrument in a radial direction with respect to the curved track.

Conveniently, at least one of the control elements further comprises one or more relays adapted to receive the respective control signal and actuate one of the driving arrangements.

Advantageously, the control assembly further comprises a user operated control unit adapted to house the control elements.

Preferably, the three degrees of freedom of movement are substantially confocal in free space around a fixed point.

Conveniently, each driving assembly operates with only one degree of freedom.

Another aspect of the present invention provides a method of manufacturing a control assembly for manipulating the movement of an endoscopic instrument. The method comprises: providing an endoscopic instrument mounting arrangement adapted to receive an endoscopic instrument and offer only three independent degrees of freedom of movement of an endoscopic instrument received by the arrangement, each degree of freedom of movement being about or along a respective axis; providing three driving arrangements each being configured to drive the endoscopic instrument in only one of the degrees of freedom of movement; and providing three independent control elements configured to receive user input, such that the actuation of each of the three independent control elements regulates one of three corresponding control signals which each control a respective one of the driving arrangements independently of the other two driving arrangements in accordance with the user input.

Advantageously, the endoscopic instrument is an endoscope.

Preferably, the step of providing the endoscopic instrument mounting arrangement comprises: providing a curved track which is configured so as to be rotatable about a rotation axis with respect to a support structure of the control assembly, the curved track having a center of curvature along the rotation axis; and providing an endoscopic instrument mount configured to receive an endoscopic instrument, move along the curved track, and move the instrument in a radial direction with respect to the curved track.

Conveniently, the step of providing the three control elements further comprises the step of providing at least one of the control elements with one or more relays adapted to receive the one or more control signals and actuate one of the driving arrangements.

Advantageously, the method further comprises the step of providing a user operated control unit adapted to house the control elements.

Preferably, the step of providing an endoscopic instrument mounting arrangement comprises providing an endoscopic instrument mounting arrangement in which the three degrees of freedom of movement are substantially confocal in free space about a fixed point.

BRIEF DESCRIPTION OF THE SEVERAL VIEWS OF THE DRAWINGS

In order that the present invention may be more readily understood, embodiments thereof shall be described, by way of example, with reference to the accompanying drawings.

DETAILED DESCRIPTION OF THE INVENTION

Figure 1:
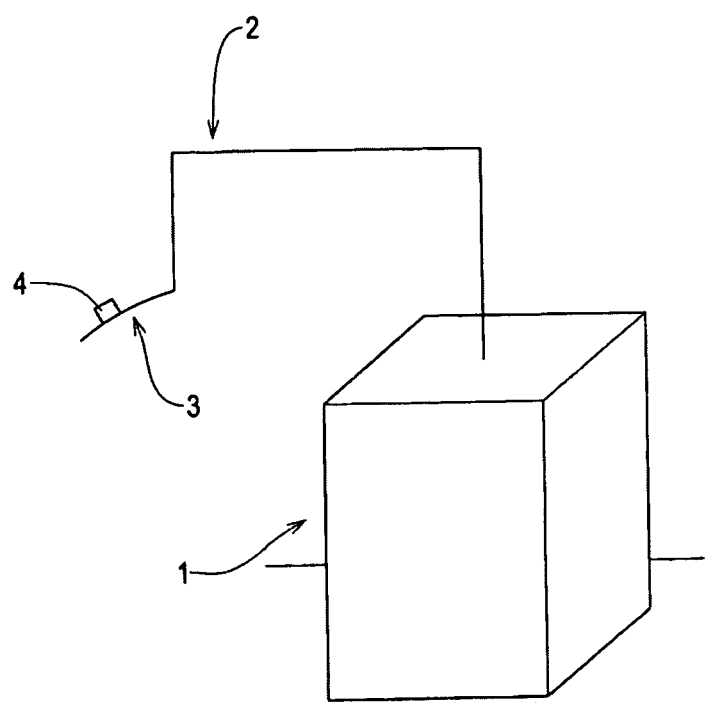
FIG. 1 shows a schematic view of the control assembly according to an embodiment of the present invention.

An example control assembly 1 for controlling the movement of an endoscope 6 according to an embodiment of the present invention is shown in FIG. 1. Preferably, the control assembly 1 is a mechotronic assembly.

Figure 2:
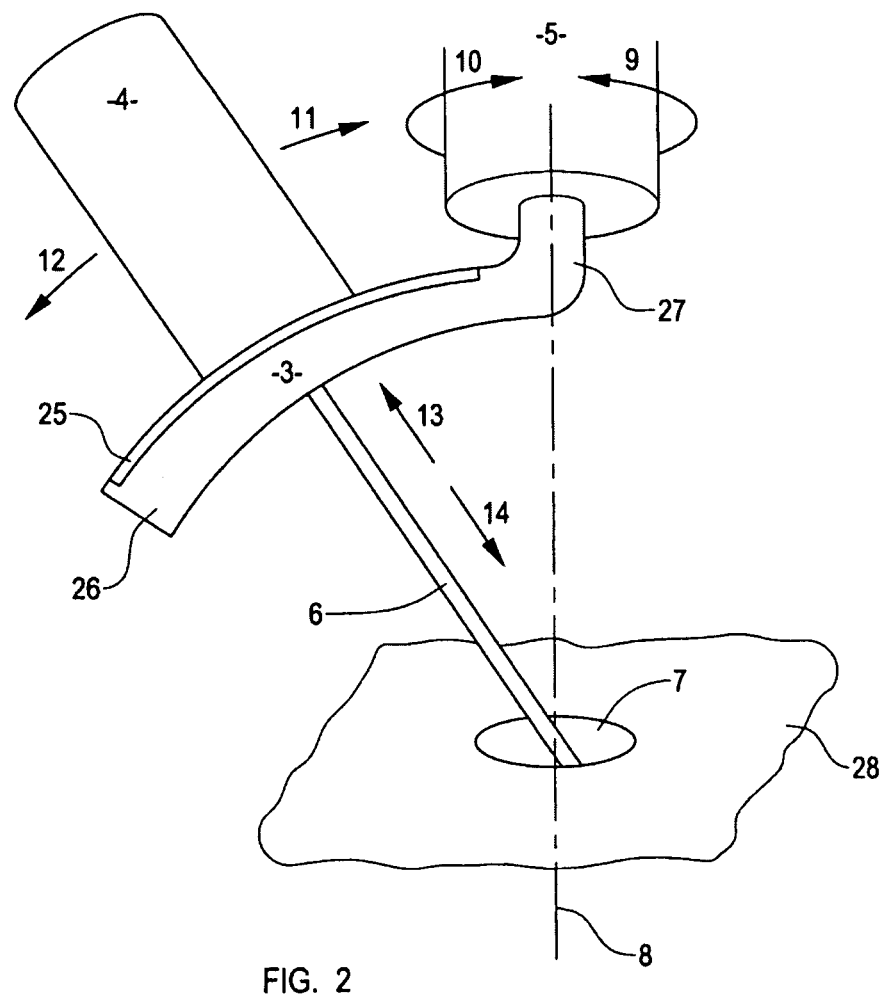
FIG. 2 shows a schematic view of part of a control assembly according to an embodiment of the present invention.

As seen more readily in the view of the portion of the control assembly 1 shown in FIG. 2, the control assembly 1 comprises a support structure 2 adapted to support a curved arm 3. The support structure 2 and curved arm 3 are configured such that the curved arm 3 may rotate with respect to the support structure 2 about a vertical axis 8.

The support structure 2 includes a mounting member 5 adapted to secure the curved arm 3 with respect to the rest of the support structure 2. In order to allow the curved arm 3 to be rotated with respect to the support structure 2, the mounting member 5 may include one or more motors (not shown) which are configured to drive the clockwise 9 or anticlockwise 10 rotation of the curved arm 3 with respect to the mounting member 5. Alternatively, one or more motors (not shown) may be provided to rotate the mounting member 5 with respect to the rest of the support structure 2.

The curved arm 3 is adapted to carry an endoscope mount 4 which may move with respect to the curved arm 3. To this end, the curved arm 3 may include a curved track 25. The endoscope mount 4 is configured such that it may move up 11 and down 12 the track 25 between a distal end 26 and a proximal end 27 of the curved arm 3 (where the curved arm 3 is operable to rotate with respect to the support structure about a vertical axis towards the proximal end 27 of the arm 3).

The track 25 may, for example, include a number of teeth (not shown) which are sized and positioned to mate with corresponding rotor teeth (not shown) which are associated with the endoscope mount 4.

The curved arm 3 has a degree of curvature which is centered at a point which is along the vertical axis 8 about which the arm 3 rotates with respect to the support structure 2. In other words, the curved arm 3 is a segment of a circle which has a center point along the vertical axis 8.

The endoscope mount 4 includes a mechanism to mate with the curved arm 3 and this mechanism may comprise one or more rotors with rotor teeth (as described above). One or more motors (not shown) may be housed in the endoscope mount 4, and these motors may be linked to the one or more rotors, such that the rotors may be driven in a rotational manner to cause the endoscope mount 4 to move along the curved arm 3.

The endoscope mount 4 is configured to allow the attachment of an endoscope 6 thereto. The endoscope mount 4 may include two or more gripping members (not shown) resiliently biased towards each other and between which an endoscope shaft may be received. Thus, the two or more gripping members are capable of holding an endoscope 6. The two or more gripping members are moveable with respect to the curved arm 3 such that the endoscope 6 may be moved in an upwards 13 or downwards 14 direction with respect thereto (i.e. a radial direction with respect to the curved arm 3). The two or more gripping members may rotate to pass achieve the aforementioned movement of the endoscope 6.

The gripping members are preferably provided with a surface which is suitable to grip the shaft of an endoscope 6 (this may be by friction, static friction, or engagement of corresponding attachment fixtures—not shown).

One or more motors (not shown) are provided in the endoscope mount 4 to drive movement of a endoscope 6 fitted thereto in the upward 13 and downward 14 directions with respect to the curved arm 3.

Collectively, the curved arm 3, and the endoscope mount 4 comprise an endoscope mounting arrangement. In an embodiment, it is the endoscope mounting arrangement which has three degrees of freedom of movement with respect to the support structure 2.

It will be appreciated that the arm 3 need not be curved; however, the arm should include a track 25 which allows the endoscope mount 4 to be driven along the track 25 along the line of a curve (the curve being as described above in relation to the curved arm 3).

A control unit 15 may be provided for connection to a control unit interface (not shown) of the control assembly 1. The control unit 15 may take any number of different forms including a unit which comprises switches which are voice activated, a unit which comprises switches actuated by foot pedals, a unit which comprises switches activated by head movements, or a unit which comprises switches which are actuated by a combination of user inputs. The control unit 15 may form part of the control assembly 1 or may be a separate unit 15.

Figure 3:
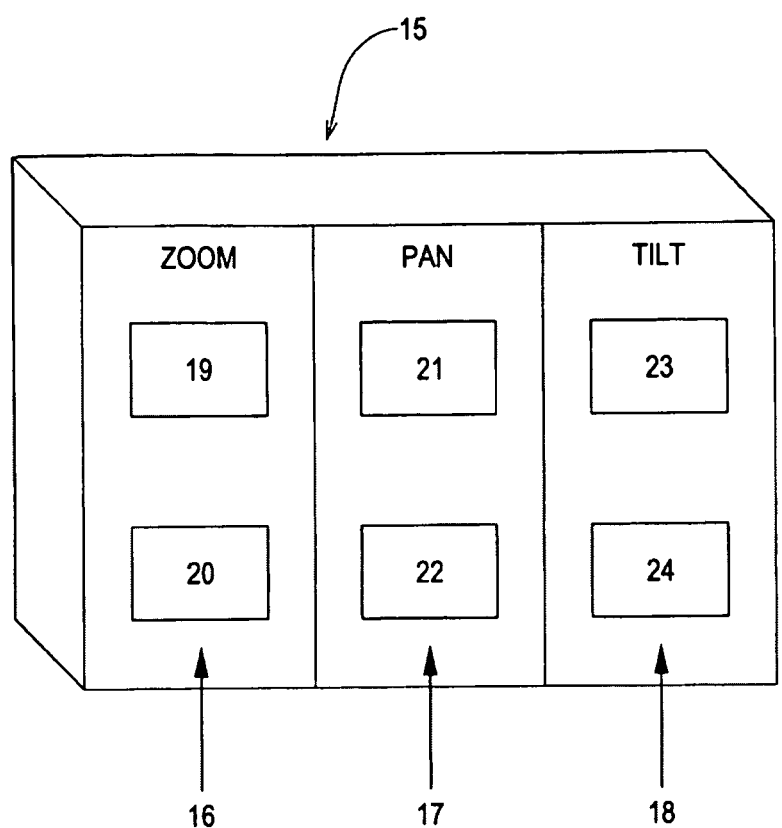
FIG. 3 shows a schematic view of a controller for a control assembly according to an embodiment of the present invention.

An example control unit 15 is shown in FIG. 3. The unit includes three pairs 16,17,18 of switches 19,20,21,22,23,24. The switches are coupled to motors in the control assembly 1 and are configured to actuate the motors to control movement of the control assembly 1. No computation (e.g. kinematic calculations) is required between a user input to the control unit 15 and the actuation of the motors (as such, control of the control assembly is so called "direct" control). A first pair 16 of the switches 19,20 actuate one or more motors in the endoscope mount 4 to move an endoscope 6 mounted thereon in an upward 13 or downward 14 direction with respect to the curved arm 3. A second pair 17 of the switches 21,22 actuate one or more motors which are arranged to rotate the curved arm 3 with respect to the support structure 2. A third pair 18 of the switches 23,24 actuate one or more motors which drive the endoscope mount 4 along the curved arm 3.

In each pair 16,17,18 of switches 19-24 one switch controls driving of the control assembly 1 in a first manner and the other switch controls driving of the control assembly 1 in the opposing manner.

Each pair of switches 16,17,18 constitutes a control element each of which is capable of affecting, regulating or otherwise altering or actuating a respective control signal. The control elements are independent in that actuation or use of one control element does not actuate or use another control element.

Each switch 19-24 is preferably connected to a respective relay (not shown) or to a relay (not shown) for each pair 16,17,18 of switches. The relays, when actuated by the switches 19-24 are operable to allow current to pass from a power supply (not shown) toward the motors in the control assembly 1 or to discontinue or reverse the follow of current (as the case may be).

The control unit 15 may be wirelessly connected to the control assembly 1 or may be connected by a wire or both.

The control unit 15 may be connected to the control assembly 1 through an interface (not shown).

The control signals which are actuated or otherwise affected by the control unit 15 are each capable of controlling a respective driving arrangement independently of the other driving arrangements. The driving arrangements may form part of the endoscope mount arrangement or may be fitted thereto.

Preferably, each driving arrangement operates with only one degree of freedom, in that it causes movement (not only of an endoscopic instrument which is held by the control assembly 1, but of components of the control assembly 1) about or along only one axis, and does not cause a compound movement of different parts of the control assembly 1 which results in a movement of the endoscopic instrument in one degree of freedom. Advantageously, each driving arrangement comprises only a single motor or other actuator.

The control assembly 1, therefore, has three degrees of freedom of movement: a first degree of freedom of movement (pan) is provided by the rotation of the curved arm 3 about the vertical axis 8 with respect to the support structure 2; a second degree of freedom of movement (tilt) is provided by movement of the endoscope mount 4 along the curved arm 3; and a third degree of freedom of movement (zoom) is provided by movement of an endoscope 6 mounted on the endoscope mount 4 in an upward or downward direction with respect to the curved arm 3.

Pan, tilt and zoom movement may be achieved using one motor for each degree of movement or using pairs of motors (each to drive movement in opposing directions). Additional redundant motors may be provided for use in the event of failure of one or more of the motors. One or more gearboxes may be provided for use with the motors. Each group of motors associated with a particular movement comprise a driving arrangement of that movement. One or more gearboxes may form part of the driving arrangements.

One or more encoders (for example encoder wheels and readers) may be provided for each degree of freedom of movement to measure the amount of movement.

In operation, the control assembly 1 may be positioned with respect to a patient 28 or other object to be operated on. The control assembly 1 is positioned such that the support structure 2 supports the curved arm 3 above an incision 7 in the patient 28. The vertical axis 8 about which the curved arm 3 rotates with respect to the support structure 2 is aligned with the incision 7. The distance between the curved arm 3 and the incision 7 is adjusted such that the curvature of the arm 3 is substantially centered at the incision 7 (this is to ensure confocal movement about the incision 7 or sufficiently confocal movement about the incision 7 to allow only an acceptable amount of stretching or movement of the incision 7).

An endoscope 6 is mounted to the endoscope mount 4 of the control assembly 1 and inserted into the incision 7. Thus, the endoscope 6 (which is a substantially straight member) follows a radial line from the incision to the curved arm 3.

Movement of the control assembly 1 is only possible in the above described three degrees of freedom of movement. All three of these degrees of freedom of movement are centered on a common point which is located substantially at the incision 7 when the control assembly 1 is correctly positioned. In addition, all three degrees of freedom of movement are orthogonal with respect to each other such that movement in one degree will not cause movement in another. Thus, all possible movements of the control assembly 1 (and, more particularly, an endoscope received by the control assembly 1) are confocal about that point.

Movement of an endoscope 6 mounted on the endoscope mount 4 is, therefore, such that the endoscope 6 passes through the incision and can be safely moved in all three degrees of freedom of movement without a risk of harming the patient 28 by stretching or tearing the incision 7. As such no expensive and bulky computing devices need be utilized in order to drive the control assembly 1.

The confocal movement is preferably substantially confocal in free space (i.e. when movement is not restricted by any physical barriers such as the internal wall of an aperture through which an endoscopic instrument 6 mounted on the endoscope mount 4 is passed).

The control unit 15 is functional such that a user (e.g. a surgeon) moves an endoscope 6 mounted on the endoscope mount 4 by driving the motors of the control assembly 1 directly to control the pan, tilt and zoom.

Moreover, the view of the patient 28 captured by the endoscope will not rotate (about a longitudinal axis of the endoscope 6) and will always be in the same orientation (because the endoscope 6 does not rotate with respect to the endoscope mount 4). Therefore, a surgeon (or other user) is not required to adjust the view to compensate for rotational movement (as in many prior art devices).

It will be appreciated that a control assembly 1 according to embodiments of the present invention can provide a kinematically complete range of movement for an endoscope 6 mounted thereon (in other words, the endoscope can be moved to view any area within a body which would have been possible had the endoscope been held and manoeuvred by a surgeon or his assistant). There is no requirement for complex computations to be carried out and every movement of the endoscope 6 can be achieved by a direct actuation of the relevant motor or motors by the user. The described control assembly 1 is much simpler in operation and design; this results in reduced manufacturing and operating costs. Moreover, the control assembly 1 is safer than prior robots because, when correctly positioned, it is not capable of movement which is not confocal with the incision 7 in a patient 28. The control assembly 1 can be smaller in size and thus use less space in an operating theater (which is often in high demand).

The invention has been described in relation to an endoscope 6; however, it will be understood that the invention can equally be used with other endoscopic instruments.

It will be appreciated that the above described control assembly 1 is not only useful for surgery but can be utilized in many industrial fields where a view of a location with limited access is required.

When used in this specification and claims, the terms "comprises" and "comprising" and variations thereof mean that the specified features, steps or integers are included. The terms are not to be interpreted to exclude the presence of other features, steps or components.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

I claim:

1. A control assembly for manipulating a movement of an endoscopic instrument, the control assembly comprising:
   a support structure including a mounting member;
   an endoscopic instrument mounting arrangement adapted to receive the endoscopic instrument and offer only three independent degrees of freedom of movement of the endoscopic instrument received by the arrangement, each degree of freedom of movement being about or along a respective axis;
   three driving arrangements, each being configured to drive the endoscopic instrument in only one of the degrees of freedom of movement and each driving arrangement including a motor; and
   a control unit including three pairs of switches providing three independent control elements configured to receive user input, the switches being coupled to the motors to control movement of the control assembly, such that the actuation of each of the three independent control elements regulates one of three corresponding control signals which each control a respective one of the driving arrangements independently of the other two driving arrangements in accordance with the user input by direct control of the driving arrangement based on the user input without kinematic calculations, wherein the endoscopic instrument mounting arrangement comprises:
      a curved arm including a curved track secured by the mounting member to the support structure, the curved track being configured so as to be rotatable about a vertical rotation axis with respect to the support structure of the control assembly to provide a pan movement, the curved track having a center of curvature along the vertical rotation axis; and
      an endoscopic instrument mount configured to receive an endoscopic instrument, move along the curved track to provide a tilt movement, and move the instrument in a radial direction with respect to the curved track to provide a zoom movement,
      the three degrees of freedom of movement are substantially confocal in free space around a fixed point, such that, in use, the control assembly is positioned with respect to a patient, the support structure supports the curved arm above an incision in the patient, and the vertical rotation axis is aligned with the incision, with the center of curvature of the curved track being centered on the incision and the instrument positioned along a radial line from the incision to the curved arm to provide confocal movement about the incision, and
      the curved arm being suspended beneath the mounting member.

2. The control assembly according to claim 1 wherein the endoscopic instrument is an endoscope.

3. The control assembly according to claim 1, wherein at least one of the control elements further comprises one or more relays adapted to receive the respective control signal and actuate one of the driving arrangements.

4. The control assembly according to claim 1, wherein each driving assembly operates with only one degree of freedom.

5. The control assembly of claim 1, wherein the independent control elements each comprise switches activatable by head movements.

6. The control assembly of claim 1, wherein the curved track includes a number of teeth which are configured to mate with corresponding teeth associated with the endoscopic instrument mount.

7. A method of manufacturing a control assembly for manipulating a movement of an endoscopic instrument, the method comprising:
provproviding a support structure including a mounting member;
providing an endoscopic instrument mounting arrangement adapted to receive the endoscopic instrument and offer only three independent degrees of freedom of movement of the endoscopic instrument received by the arrangement, each degree of freedom of movement being about or along a respective axis;
providing three driving arrangements each being configured to drive the endoscopic instrument in only one of the degrees of freedom of movement and each driving arrangement including a motor; and
providing a control unit including three pairs of switches providing three independent control elements configured to receive user input, the switches being coupled to the motors to control movement of the control assembly, such that the actuation of each of the three independent control elements regulates one of three corresponding control signals which each control a respective one of the driving arrangements independently of the other two driving arrangements in accordance with the user input by direct control of the driving arrangement based on the user input without kinematic calculations, wherein the endoscopic instrument mounting arrangement comprises:
a curved arm including a curved track secured by the mounting member to the support structure, the curved track being configured so as to be rotatable about a vertical rotation axis with respect to the support structure of the control assembly to provide a pan movement, the curved track having a center of curvature along the vertical rotation axis; and
an endoscopic instrument mount configured to receive an endoscopic instrument, move along the curved track to provide a tilt movement, and move the instrument in a radial direction with respect to the curved track to provide a zoom movement,
the three degrees of freedom of movement are substantially confocal in free space around a fixed point, such that, in use, the control assembly is positioned with respect to a patient, the support structure supports the curved arm above an incision in the patient, and the vertical rotation axis is aligned with the incision, with the center of curvature of the curved track being centered on the incision and the instrument positioned along a radial line from the incision to the curved arm to provide confocal movement about the incision, and
the curved arm being suspended beneath the mounting member.

8. The method according to claim 7 wherein the endoscopic instrument is an endoscope.

9. The method according to claim 7, wherein the step of providing the three control elements further comprises:
providing at least one of the control elements with one or more relays adapted to receive the one or more control signals and actuate one of the driving arrangements.

10. The method of claim 7, wherein the independent control elements each comprise switches activatable by head movements.

* * * * *